United States Patent
Wang et al.

(10) Patent No.: US 11,580,637 B2
(45) Date of Patent: Feb. 14, 2023

(54) METHOD FOR DETECTING IMAGE OF OBJECT USING CONVOLUTIONAL NEURAL NETWORK

(71) Applicant: NATIONAL CHUNG CHENG UNIVERSITY, Chiayi County (TW)

(72) Inventors: Hsiang-Chen Wang, Chiayi (TW); Hao-Yi Syu, Chiayi County (TW); Tsung-Yu Yang, Chiayi County (TW); Yu-Sheng Chi, Chiayi County (TW)

(73) Assignee: National Chung Cheng University, Chiayi County (TW)

( * ) Notice: Subject to any disclaimer, the term of this patent is extended or adjusted under 35 U.S.C. 154(b) by 214 days.

(21) Appl. No.: 17/081,172

(22) Filed: Oct. 27, 2020

(65) Prior Publication Data
US 2021/0374949 A1 Dec. 2, 2021

(30) Foreign Application Priority Data
Jun. 1, 2020 (TW) .................. 109118361

(51) Int. Cl.
*G06T 7/00* (2017.01)
*G16H 30/40* (2018.01)
(Continued)

(52) U.S. Cl.
CPC .......... *G06T 7/0012* (2013.01); *G06F 16/55* (2019.01); *G06N 3/08* (2013.01); *G16H 30/20* (2018.01);
(Continued)

(58) Field of Classification Search
CPC ......... G06T 7/0012; G06T 2207/10081; G06T 2207/10116; G16H 30/20; G16H 30/40; G16H 50/20; G06F 16/55; G06N 3/08
See application file for complete search history.

(56) References Cited

U.S. PATENT DOCUMENTS 10,755,142 B2 * 8/2020 Saliou .................. G06V 10/255
2019/0114804 A1 * 4/2019 Sundaresan .......... G06V 30/194
(Continued)

OTHER PUBLICATIONS

M. Liu, J. Jiang and Z. Wang, "Colonic Polyp Detection in Endoscopic Videos With Single Shot Detection Based Deep Convolutional Neural Network," in IEEE Access, vol. 7, pp. 75058-75066, 2019, doi: 10.1109/ACCESS.2019.2921027 (Year: 2019).*
(Continued)

*Primary Examiner* — Vu Le
*Assistant Examiner* — Julius Chai
(74) *Attorney, Agent, or Firm* — Rosenberg, Klein & Lee (57) ABSTRACT

The present application related to a method for detecting an object image using a convolutional neural network. Firstly, obtaining feature images by Convolution kernel, and then positioning an image of an object under detected by a default box and a boundary box from the feature image. By Comparing with the sample image, the detected object image is classifying to an esophageal cancer image or a non-esophageal cancer image. Thus, detecting an input image from the image capturing device by the convolutional neural network to judge if the input image is the esophageal cancer image for helping the doctor to interpret the detected object image.

7 Claims, 12 Drawing Sheets

(51) Int. Cl.
*G16H 30/20* (2018.01)
*G06N 3/08* (2006.01)
*G06F 16/55* (2019.01)
*G16H 50/20* (2018.01)

(52) U.S. Cl.
CPC ............ *G16H 30/40* (2018.01); *G16H 50/20* (2018.01); *G06T 2207/10081* (2013.01); *G06T 2207/10116* (2013.01)

(56) References Cited

U.S. PATENT DOCUMENTS

| | | | |
|---|---|---|---|
| 2019/0205643 A1* | 7/2019 | Liu ........................ | G06V 20/00 |
| 2020/0027207 A1* | 1/2020 | Zhang .................... | G06V 10/82 |
| 2021/0082181 A1* | 3/2021 | Shi ........................ | G06V 20/64 |
| 2022/0036548 A1* | 2/2022 | Hu ........................ | G06V 10/95 |

OTHER PUBLICATIONS

Liu, W. et al. (2016). SSD: Single Shot MultiBox Detector. In: Leibe, B., Matas, J., Sebe, N., Welling, M. (eds) Computer Vision—ECCV 2016. ECCV 2016. Lecture Notes in Computer Science(), vol. 9905. Springer, Cham, https://doi.org/10.1007/978-3-319-46448-0_2 (Year: 2016).*

* cited by examiner

METHOD FOR DETECTING IMAGE OF OBJECT USING CONVOLUTIONAL NEURAL NETWORK

FIELD OF THE INVENTION

The present application refers to an image processing method, particularly the method in detecting an object image using the Convolutional Neural Network.

BACKGROUND OF THE INVENTION

The esophagus is a tubular organ connecting the pharynx and stomach [2], which is mainly responsible in transporting foods swallowed by the mouth to the stomach. The normal esophageal mucosa has multiple layers of squamous epithelial cells with the thickness of 200 to 500 μm; from the surface down to the bottom, the esophageal mucosa can be divided into the following layers: The mucosal epithelium (EP), lamina propria mucosal (LPM), mucosal muscularis (mm), submucosa (SM) and muscularis propria (MP). Esophageal cancer is a global top 8 most common cancer; the malignant tumors derived from epithelial tissue are called the esophageal cancer. Cancers (also known as the malignant tumors) generally affects physiological functions, the types include the sarcoma, lymphoma, leukemia, melanoma, carcinosarcoma and malignant glioma.

Among them, malignant tumors occurred in the connective tissues are called the sarcomas; the connective tissues include the fibrous tissue, adipose tissue, muscle, blood vessel, bone and cartilage. The lymphoma and leukemia occur in hematopoietic tissue. Melanomas occur in skin cells. Malignant tumors occurred in both epithelial and connective tissues are called the carcinosarcoma. Malignant gliomas are the malignant tumors occurred in the nervous tissue. The malignant tumors of esophageal carcinoma not only infiltrate the epithelial tissue of esophagus, but also the connective tissue in later stage.

At present, disease diagnosis technologies usually rely on single macro data and information, such as body temperature, blood pressure and body scan images. For example, for the detection of major diseases such as cancer, most of them are based on imaging devices including X-ray, CT scanning and nuclear magnetic resonance (NMR) imaging technology. When these diagnostic devices are used together, they are useful for the diagnosis of diseases in varying degrees. However, when these devices are used alone, they cannot carry out accurate, reliable, efficient and economic detections in the early stage of major diseases. In addition, many of these existing devices are large and invasive, such as X-ray, CT scan or nuclear magnetic resonance (NMR) imaging technology. Therefore, the endoscopy was developed to examine the presence of lesions in the digestive organs.

Early esophageal cancer is not easy to diagnose thereof. Except the fact that there are almost no symptoms in the early stage, some early esophageal cancers cannot be figured out; since the changes of these lesions are very subtle, and often just some color changes only; therefore, if the traditional endoscopy is used to detect the lesions, there will be a large number of early esophageal cancer lesions being neglected with delay treatment. Therefore, Lugol chromoendoscopy, Narrow Band Image (NBI) and Magnifying Endoscopy have been developed for lesions that are difficult to detect about.

However, the operation of endoscopy is very complicated. Before carrying out endoscopic detection, it requires medical staff to have professional licenses related to endoscopy. Moreover, the medical staff should operate the endoscope and distinguish the lesions at the same time. Even though the endoscopic detection method has been improved in many ways, it is inevitable to encounter manual operation negligence, or the endoscopic image is still not easy to identify about.

Based on the aforesaid difficulties, the present application provides a method in detecting object images by using a convolutional neural network, in which the host performs convolution operation and inputs images to the convolutional neural network to calculate and obtain the feature images, derive the images of object, and compare the sample image through the object image; classify the object images into a target object image or a non-target object image; avoid the difficulty of artificial image identification.

SUMMARY

The main purpose of the present application is to provide a method in detecting object images by using a convolutional neural network, in which the host performs convolution operation and inputs images to the convolutional neural network to calculate and obtain the feature images, derive the images of object, and compare the sample image through the object image; classify the object images into a target object image or a non-target object image; avoid the difficulty of artificial image identification.

In order to achieve the aforesaid purpose, the present application reveals a kind of convolutional neural network. Firstly, use an image capture unit to provide an input image to a host, and the input image includes at least one object image and a background image; then, the host converts the input image into plural feature values and compares the characteristic values with plural convolution kernels to obtain the partial or full corresponding characteristic values. The convolution kernels contain the characteristic values corresponding to plural partial images of at least one object image and one adjacent background image; then, the host captures at least one regional image according to the region of the partial or full of the partial or full of the characteristic values corresponding to at least one object image, generates at least one default frame according to the edge of the regional image and superimposes it on the input image, and the host matches the second center point of one of the edge boundary frames of the input image against the first center point of the default frames to obtain the center offset between the default frame and the boundary frame, so that the host can perform a regression operation based on the center offset to obtain the center offset of input image. Finally, the host compares the detected object image with at least one sample image to generate a comparison result, and then the host classifies the input image as a target object image or non-target object image according to the comparison result. Thus, the host can perform feature detection for the target object image by convolution, and then compares the object image selected in the default frame according to the sample image, and take the classified input image as the target object image or non-target object image, so as to perform automatic identification and avoid the problem of difficult identification.

The present application provides an embodiment, wherein in the step of converting the input image into a plurality of characteristic values and comparing the characteristic values with a plurality of convolution kernels to obtain at least one partial or full object image corresponding to some of the characteristic values by using the host, the host sets the detection boundary of convolution cores to 3×3×p and normalizes a plurality of pixel values of input image to a plurality of pixel normal values; the host obtains the characteristic values in a convolution layer by having the convolution kernels multiplying the pixel normal values.

The present application provides an embodiment, wherein in the step of capturing at least one regional image according to the region where the characteristic values corresponding to the partial or full detected object image, the host integrates the regions where the characteristic values are located, obtains at least one distribution region of the input image, and establishes the default frame with at least one distribution region.

The present application provides an embodiment, wherein the boundary frame corresponds to the input image, and the default frame corresponds to the detected object image.

The present application provides an embodiment, wherein in the step of Converting the input image into a plurality of characteristic values and comparing the characteristic values with a plurality of convolution kernels to obtain at least one partial or full object image corresponding to some of the characteristic values by using the host, the host convolutes each pixel of input image according to a single shot multibox detector model to detect the characteristic values.

The present application provides an embodiment, wherein in the step of performing a regression operation based on the center offset, the host performs the regression operation with a first position of the default frame, a second position of the boundary frame and a zooming factor to position the detected object image.

The present application provides an embodiment, wherein in the step of comparing the detected object image with at least one sample image by using the host, the host performs classified comparison at a fully connection layer.

The present application provides an embodiment, wherein in the step of classifying the input image as a target object image or a non-target object image based on a comparison result, when the host fails to identify the object image in the default frame that matches at least one sample image, the host classifies the input image as the non-target object image, else, the host classifies the input image as the target object image.

The present application provides an embodiment, wherein in the step of classifying the input image as a target object image or a non-target object image according to a comparison result, when the host classifies the input image as the non-target object image, the host secondly compares at least one sample image with the object image; when the host judges that the approximation of one of the detected object images is greater than the approximation threshold, it classifies the input image into the target object image; else, the host classifies the input image into the non-target object image.

DETAILED DESCRIPTION

Due to the fact of the negligence in manual operation or the difficulty of image identification caused by the complex operation of endoscopy, the present application proposes a method for detecting the object image by using the convolutional neural network, used to solve the problems of manual operation and difficulty of image identification caused by the complex operation of endoscopy.

Figure 1:
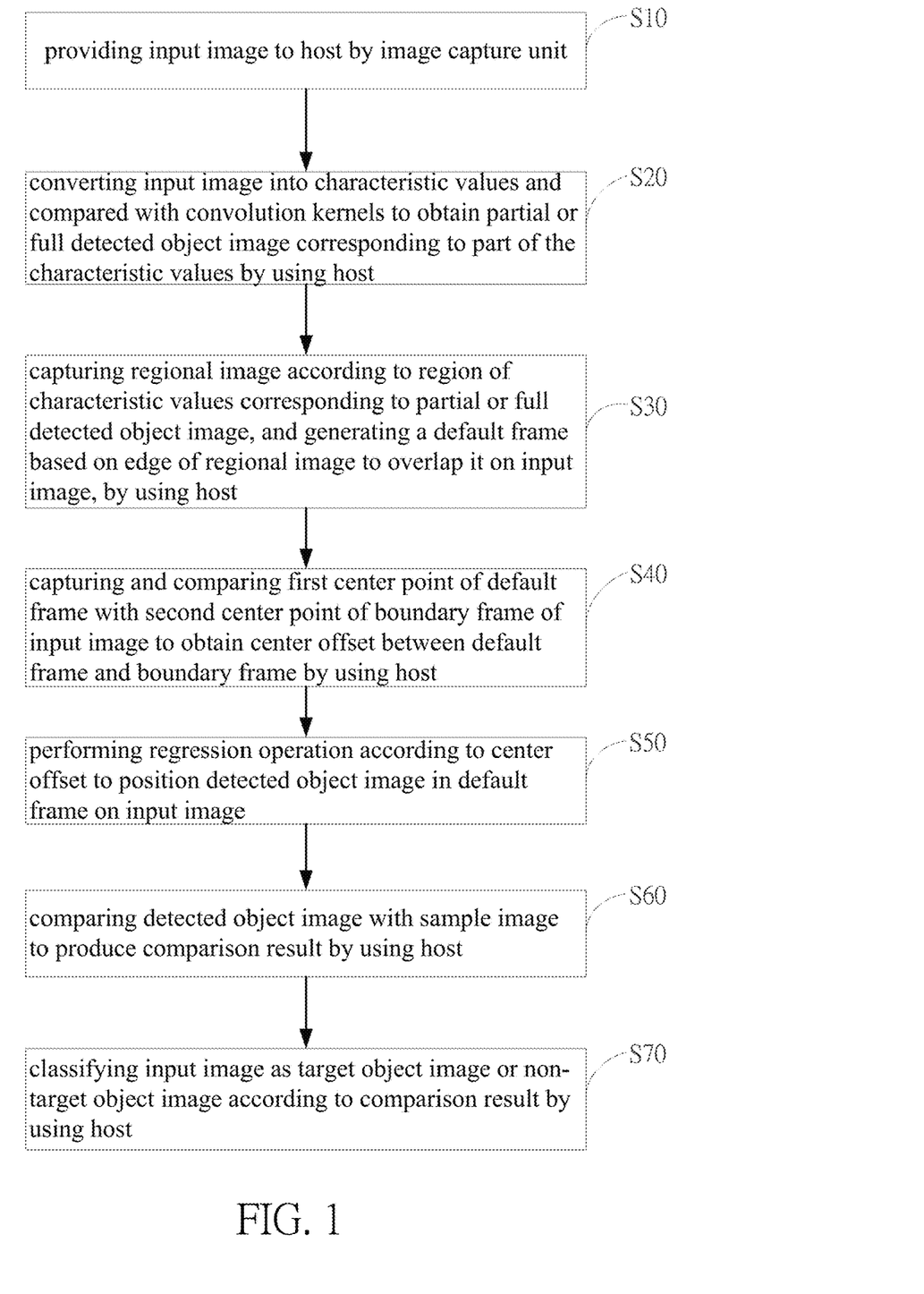
FIG. 1: which is a flowchart of convolutional image detection in the embodiment of the present application

In the following interpretation, the characteristics and matching system of a method for detecting an object image by using a convolutional neural network will be revealed as follow:

First, refer to FIG. 1, which is the flow chart of detecting an object image according to an embodiment of the present application. As shown in the figure, the steps of the method in detecting an object image with a convolutional neural network include:

Step S10: providing input image to host by image capture unit;

Step S20: converting input image into characteristic values and compared with convolution kernels to obtain partial or full detected object image corresponding to part of the characteristic values by using host;

Step S30: capturing regional image according to region of characteristic values corresponding to partial or full detected object image, and generating a default frame based on edge of regional image to overlap it on input image, by using host; and Step S40: capturing and comparing first center point of default frame with second center point of boundary frame of input image to obtain center offset between default frame and boundary frame by using host;

Step S50: performing regression operation according to center offset to position detected object image in default frame on input image;

Step S60: comparing detected object image with sample image to produce comparison result by using host; and Step S70: classifying input image as target object image or non-target object image according to comparison result by using host.

Refer to FIG. 2A to FIG. 2D, which are the detection system 1 used in the method of detecting the image of an object in the convolutional neural network of the present application; including a host 10 and an image capture unit 20. This embodiment the host 10 is served as a computer with a processing unit 12, a memory 14 and a storage unit 16 as an example, however, the present application is not limited to the embodiment; the host 10 also can be served as a server, a notebook computer, a tablet computer or an electronic device with computing capability basis. In the embodiment, the data base 30 is built in the storage unit 16, but limited to this arrangement; the data base 30 also can be set in an external storage unit of host 10. A convolution program P is executed by the processing unit 12 in the host 10, and correspondingly a convolutional neural network (CNN) is also established. Moreover, the image capture unit 20 is an endoscope in this embodiment, which is used to explore the internal organs and tissues, such as the cystoscope, gastroscope, colonoscopy, bronchoscope and laparoscope.

Figure 2A:
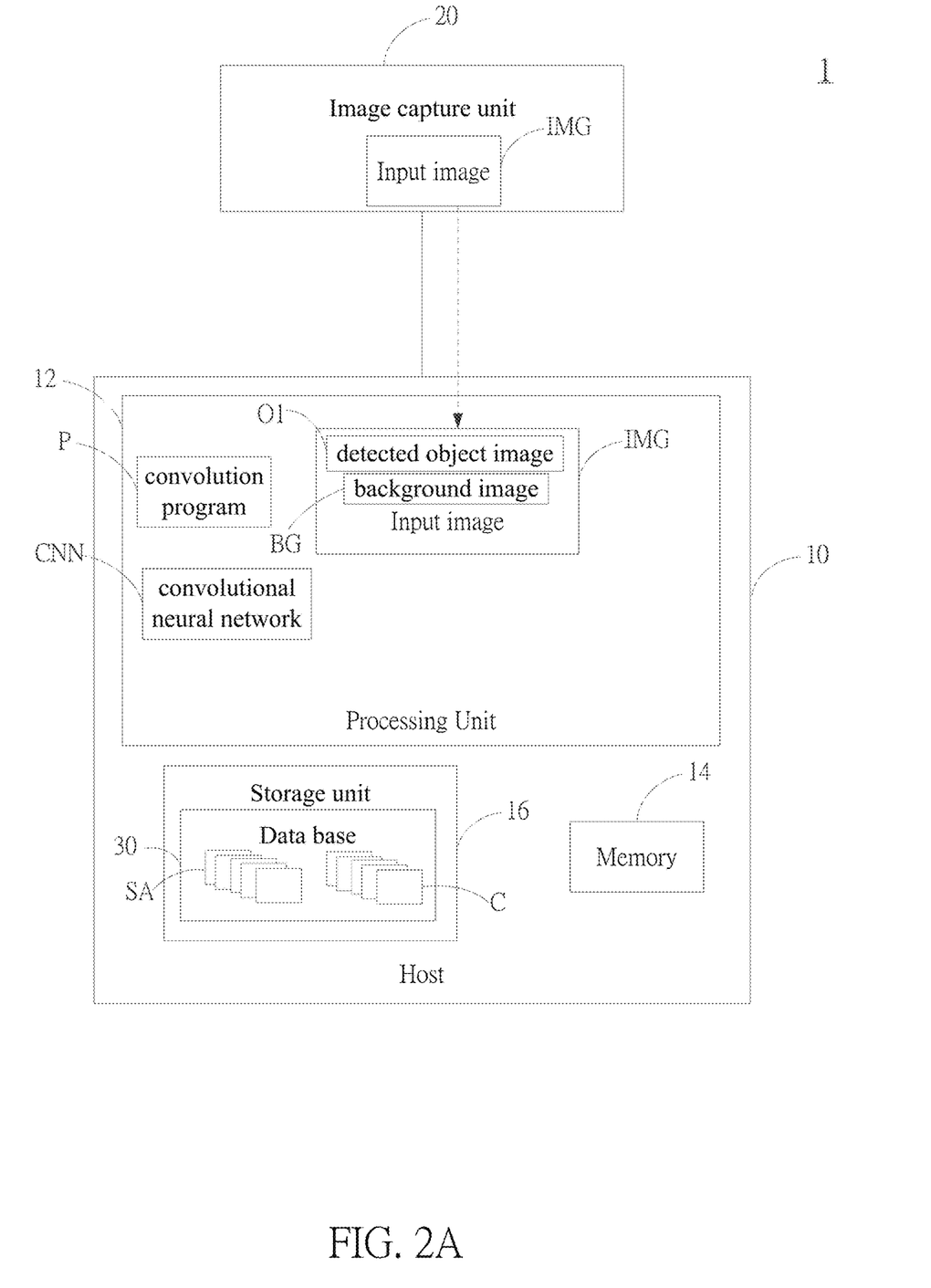
FIG. 2A to FIG. 2G: which are partial steps schematic diagrams in the first embodiment of the present application
Figure 2B:
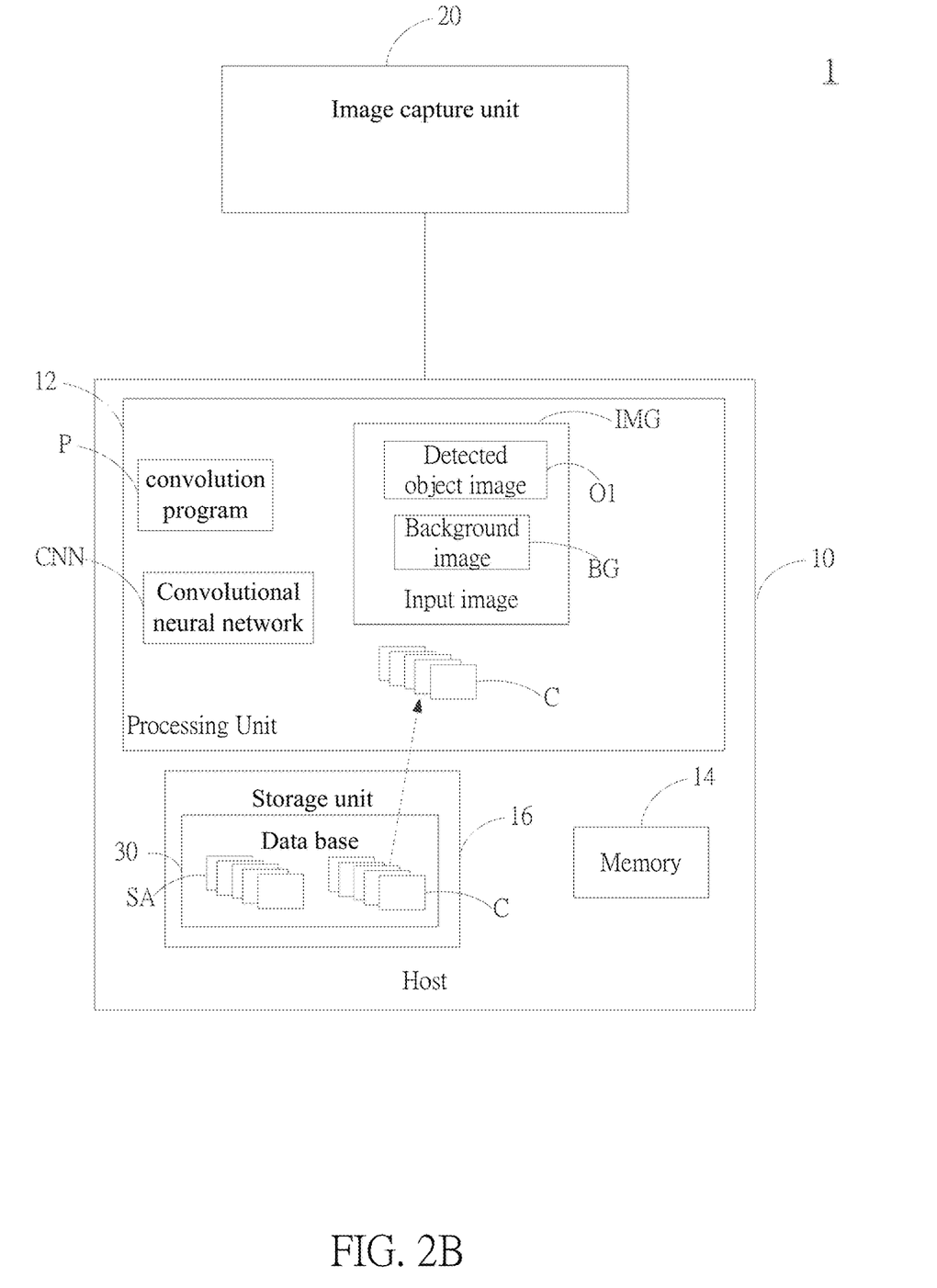
Figure 3:
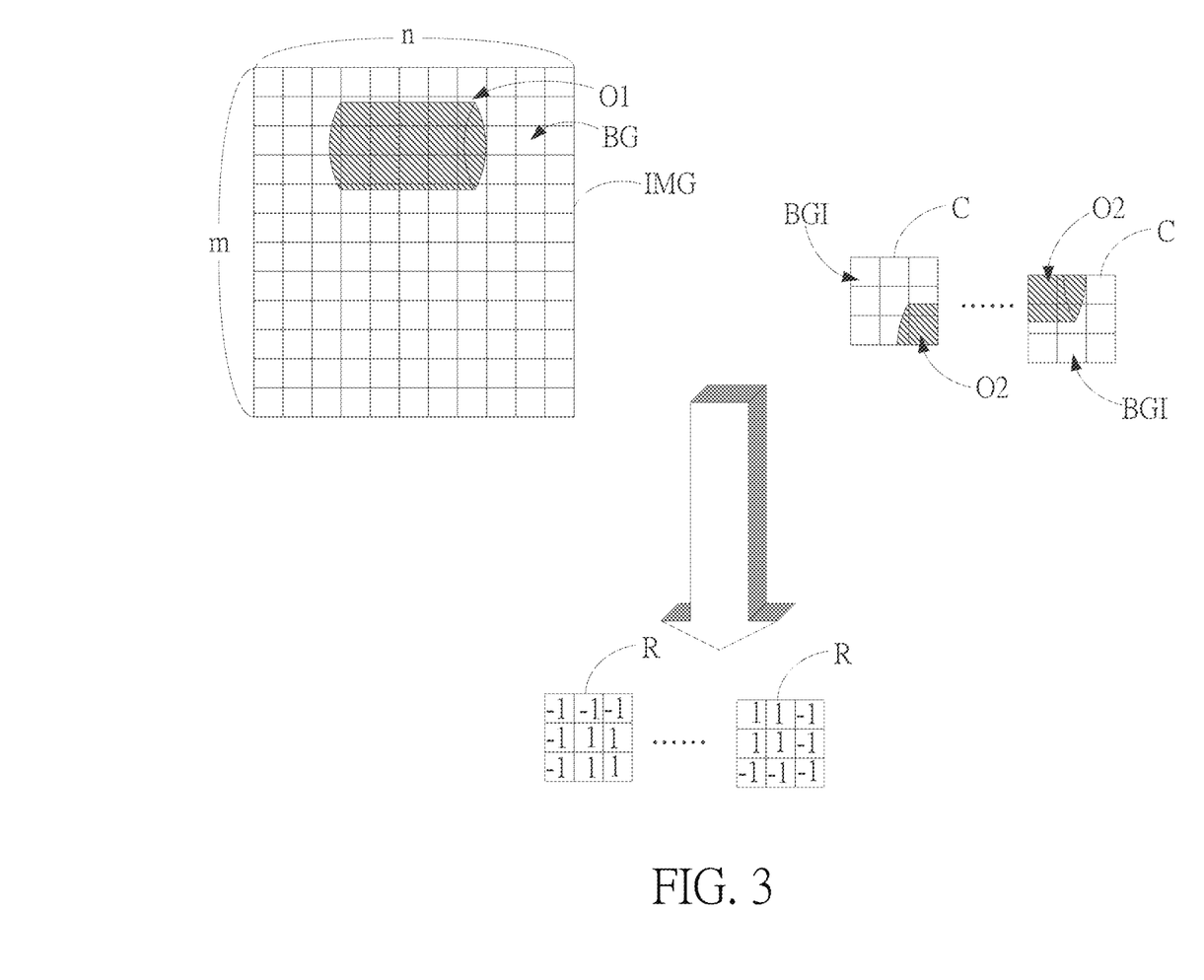
FIG. 3: which is a schematic diagram of convolution kernels and input images in the embodiment of the present application

In Step S10, as shown in FIG. 2A, the host 10 receives an input image IMG captured from the image capture unit 20, which includes at least one detected object image O1 and a background image BG; in Step S20 shown in FIG. 2B and FIG. 3, the host 10 transmits the input image IMG to each pixel unit with its own characteristic value, especially between 0 and 1; a plurality of convolution kernels C are used to detect the plural characteristic values of the input image IMG; the convolution kernels C contain the characteristic values corresponding to the plural partial image of at least one detected object image O2 and the characteristic values corresponding to the adjacent background image BGI of at least one test object, used to filter out the background image BG which does not contain the detected object image O1. Each pixel unit of the input image is convoluted by the Single Shot Multibox Detector (SSD) model to detect the characteristic values. The convolution kernel C corresponds to the corresponded characteristic value of plural partial image O2 in the detected object image O1 and the corresponded characteristic value of background image BG in the adjacent edge.

Figure 4:
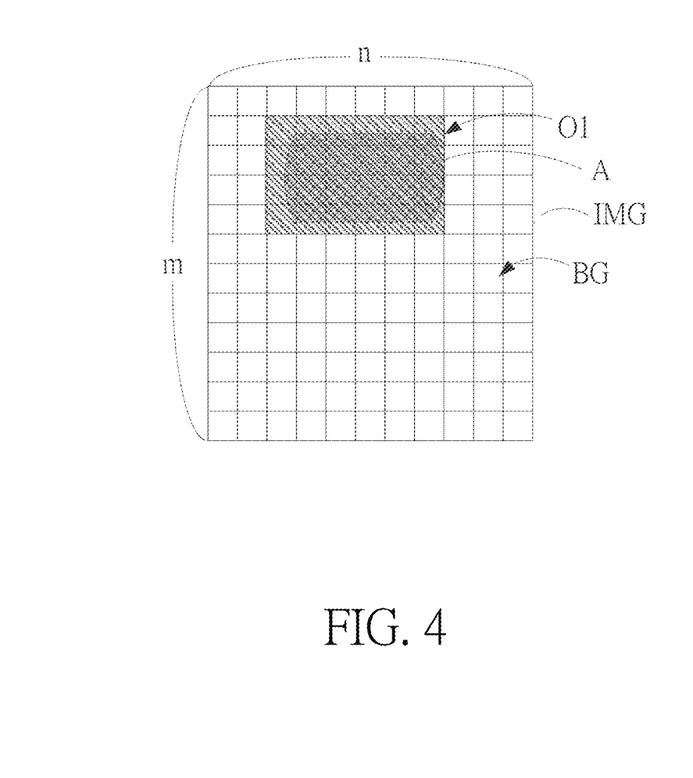
FIG. 4: which is a schematic diagram of center point in the embodiment of the present application

As shown in FIG. 3, the input image IMG is an M×N pixel unit, the convolution kernel O1 is 3×3×P units. Therefore, the convolution kernel C is used to detect the detected object image O1 and the background image BG on the input image IMG, which can reduce the processing of the background image BG in subsequent steps. The input image IMG is converted into the corresponding characteristic value through the processing unit 12, and the processing unit 12 multiplies the input image IMG through the convolution kernel C to obtain different convolution result, "1" is representing the same case and "−1" is the different case, and thus filter out the irrelevant background image B. As shown in FIG. 4, the partial or full detected object image corresponding to the partial characteristic values obtained from the input image IMG thus will obtain the location area A where the partial or full detected object image is located at.

Figure 2C:
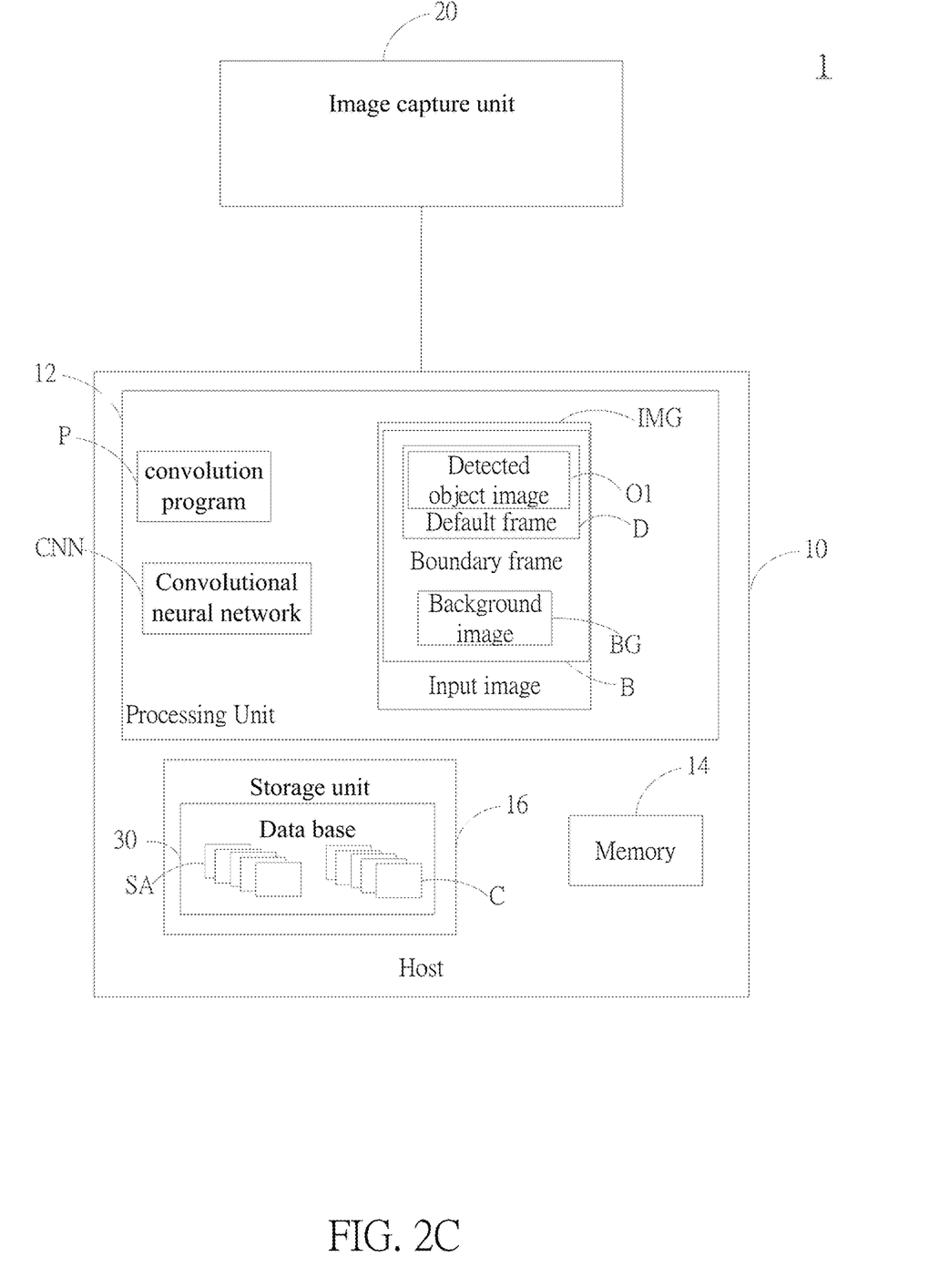
Figure 5:
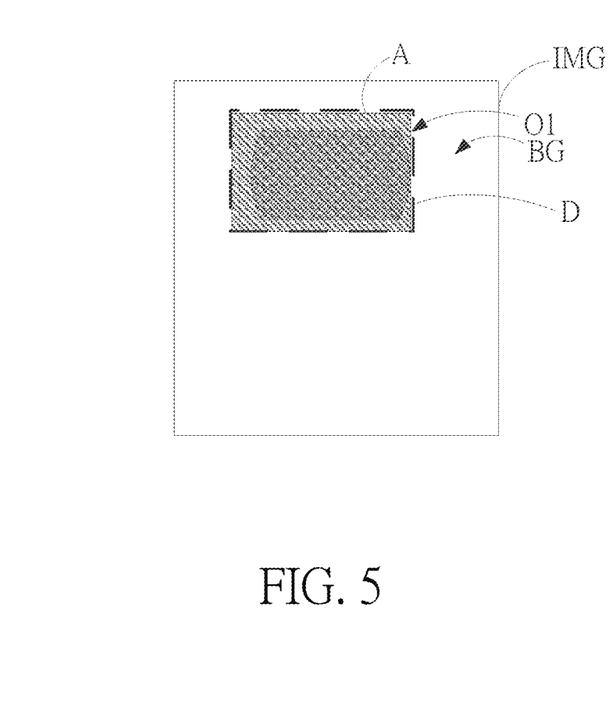
FIG. 5: which is a schematic diagram of superimposed default frame in the embodiment of the present application

As shown in FIG. 2C and FIG. 5, in Step S30, host 10 follows the location area A where the partial or full detected object image O1 locates at to obtain at least one regional image and to build the corresponded at least one default frame D and to overlap it on the input image IMG; the boundary corresponding to the input image IMG is the boundary frame B in initial, in which the size of default frame $D_{min\_size}=s_k$, the maximum size=$\sqrt{min\_size \times maxsize}$, max_size=$s_{k+1}$; the frame size $S_k$ is calculated by the following equation (1):

$$s_k = s_{min} + \frac{s_{max} - s_{min}}{m-1}(k-1), k \in [1, m]$$  Equation (1)

By using Equation (2) and (3) below, calculate the frame height and width from frame size $s_k$:

$$h_k = s_k\sqrt{a_r}$$  Equation (2)

$$w_k = s_k\sqrt{a_r}$$  Equation (3)

Where $h_k$ represents the first-check frame height of the rectangle in the $k^{th}$ characteristic diagram; the frame height, $w_k$ represents the first-checking frame width, $a_r$ represents the aspect ratio of default frame D, $a_r$>0.

Figure 2D:
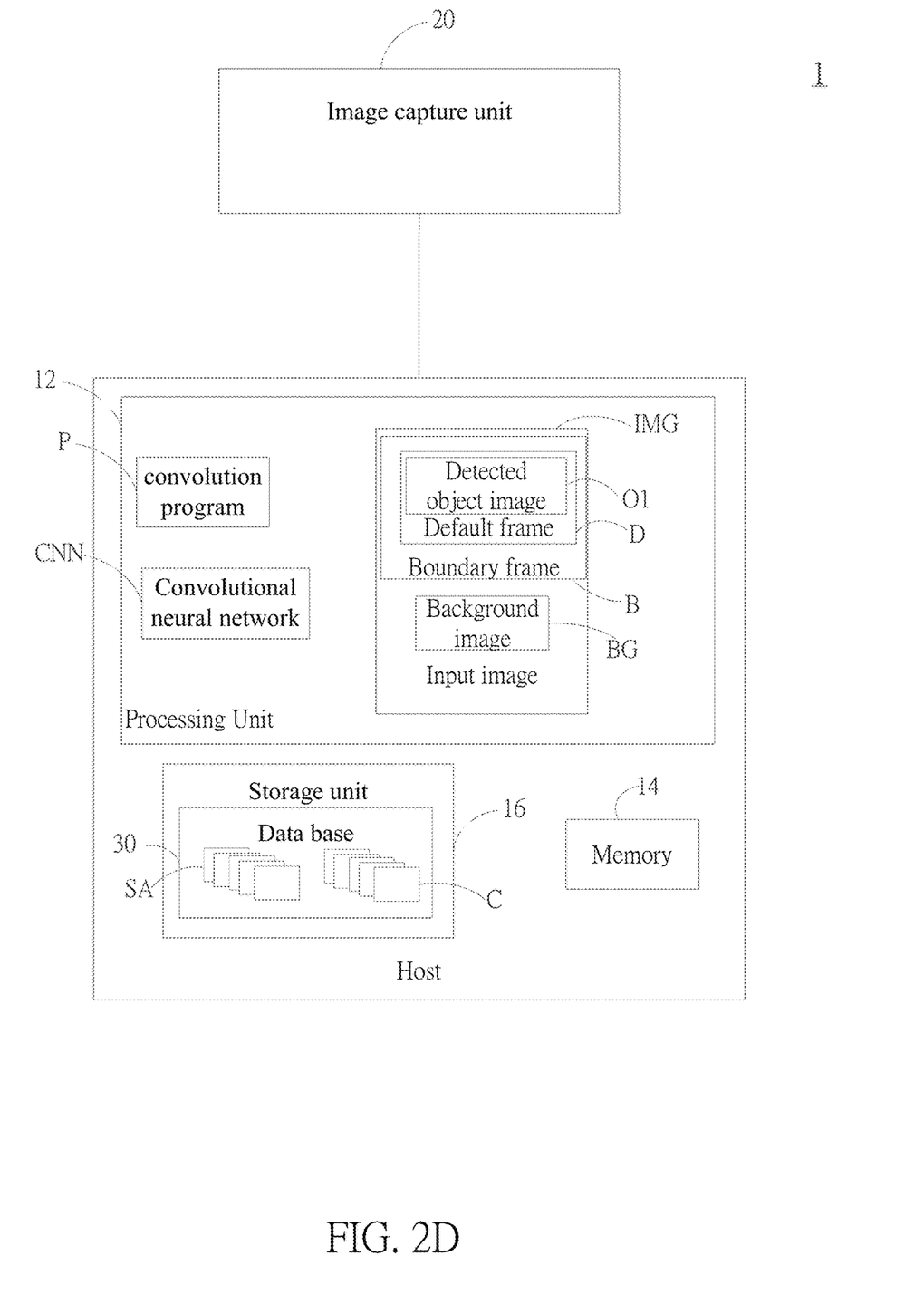
Figure 2E:
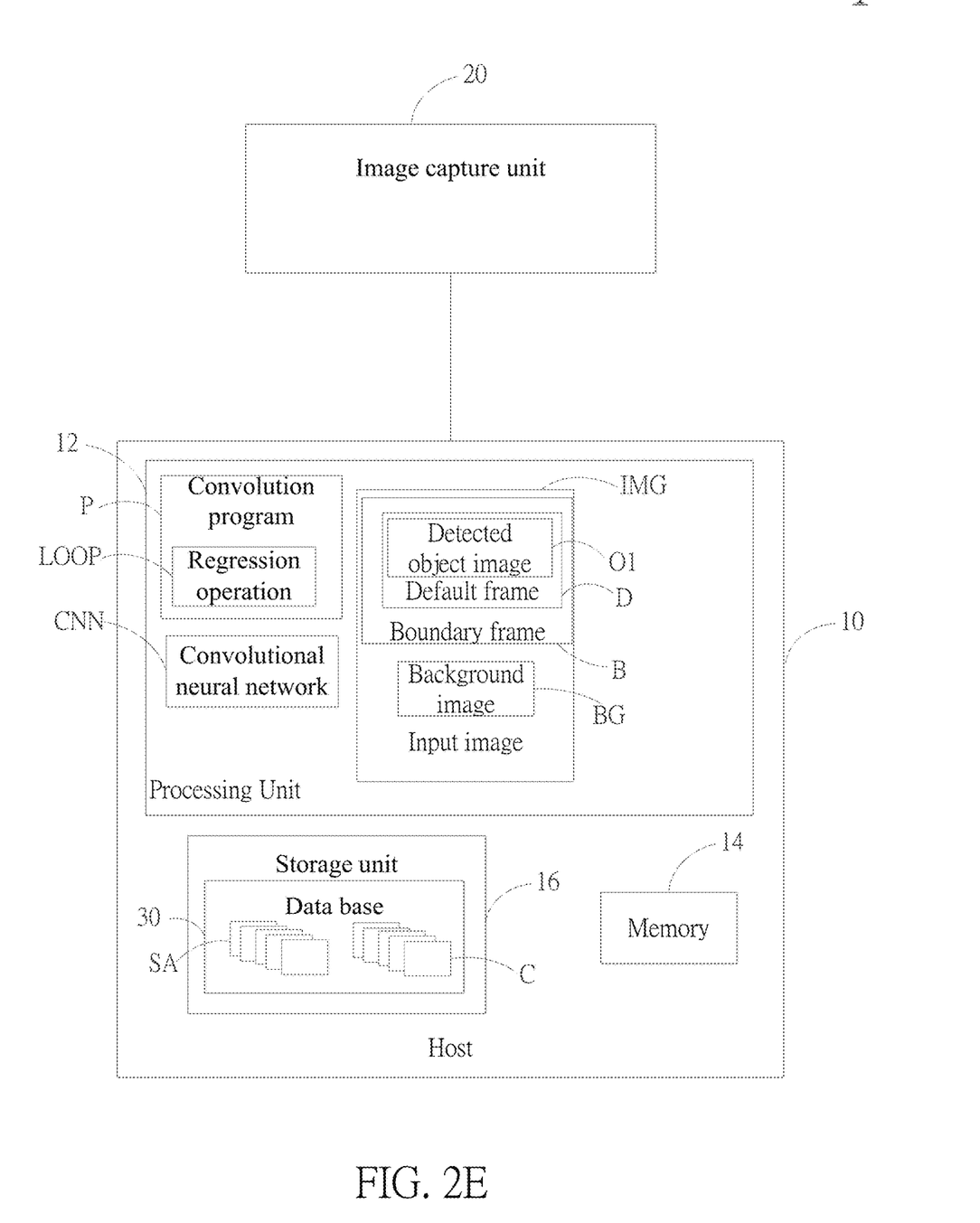
Figure 6:
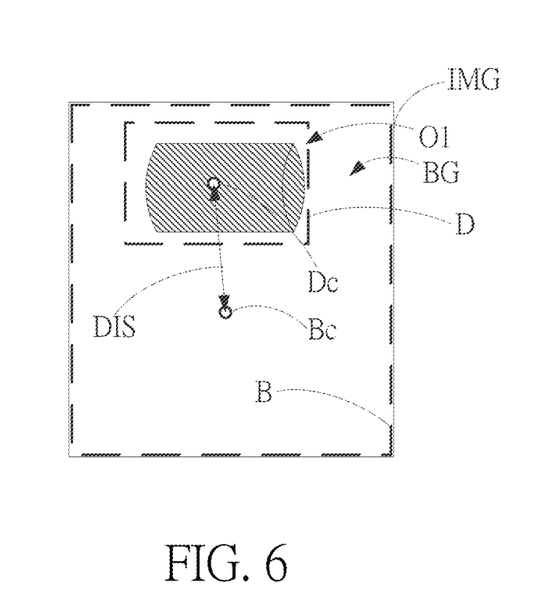
FIG. 6: which is a schematic diagram of center point offset in the embodiment of the present application
Figure 7:
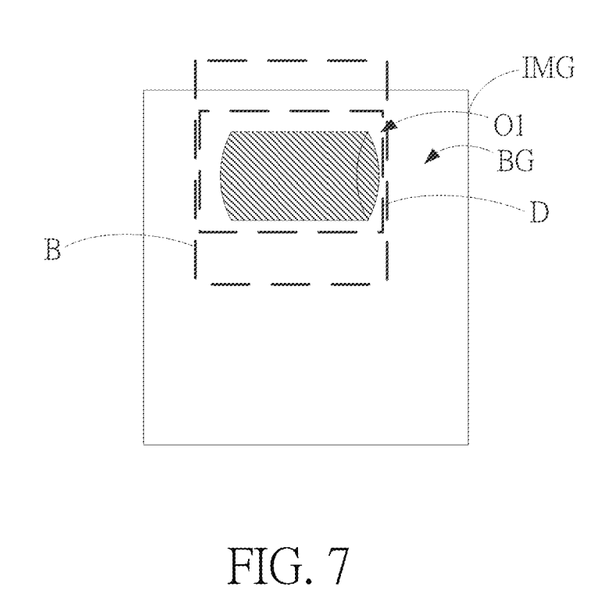
FIG. 7: which is a schematic diagram of superimposing the center points of default frame and boundary frame in the embodiment of the present application

As shown in FIG. 2D and FIG. 6, in Step S40, host 10 executes the convolutional program over the processing unit 12 by taking the first center point Dc of the default frame D and the second center point Bc at boundary frame B of the input image IMG; from the displacement between Dc and Bc, obtain the center offset. Continue to Step 50 shown in FIG. 2E and FIG. 7, host 10 uses the processing unit 12 to perform the regression operation loop according to the center point displacement DIS between the default frame D and boundary frame B; the loop running is as follows:

Location of default frame $D, d=(d^{cx},d^{cy},d^w,d^h)$  Equation (4)

Location of boundary frame $B, b=(b^{cx},b^{cy},b^w,b^h)$  Equation (5)

Zooming factor $l=(l^{cx},l^{cy},l^w,l^h)$  Equation (6)

$b^{cx}=d^w l^{cx}+d^{cx}$  Equation (7)

$b^{cy}=d^h l^{cy}+d^{cy}$  Equation (8)

$b^w=d^w \exp(l^w)$  Equation (9)

$b^h=d^h \exp(l^h)$  Equation (10)

First, align the central coordinates of boundary frame B with the central coordinates of predicting detection frame D, which means that the center point of boundary frame B is "moved" to the center point of predicting detection frame D, that is, the first center point Dc and the second center point Bc shown in FIG. 6 overlap, as shown in Equation (7) and (8); next, "zoom" the size of boundary frame to be close to the predicting detection frame D, as shown in Equation (9) and (10). After the moving and zooming, it can make the boundary frame B infinitely close to the position of the predicting detection frame D; therefore, the host 10 uses the Convolutional Neural Network (CNN) run by the convolution program executed by the processing unit 12 to consecutively and repeatedly perform the regression operation till the size of boundary frame B is infinitely close to the position of predicting detection frame D, and thus locate the relative position of detected object image O1 onto the input image IMG.

In order to more accurately define the position of the detected object image O1, a further matching of the loss equation is applied as Equation (8) in below $$L_{loc}(x,l,g)=\Sigma_{i \in Pos}^N \Sigma_{m \in \{cx,cy,w,h\}} x_{ij}^k \text{smooth}_{L1}(l_i^m - \hat{g}_j^m)$$  Equation (8)

It thus can verify the error between the position of predicting detection fame D and the detected object image O1.

Figure 2F:
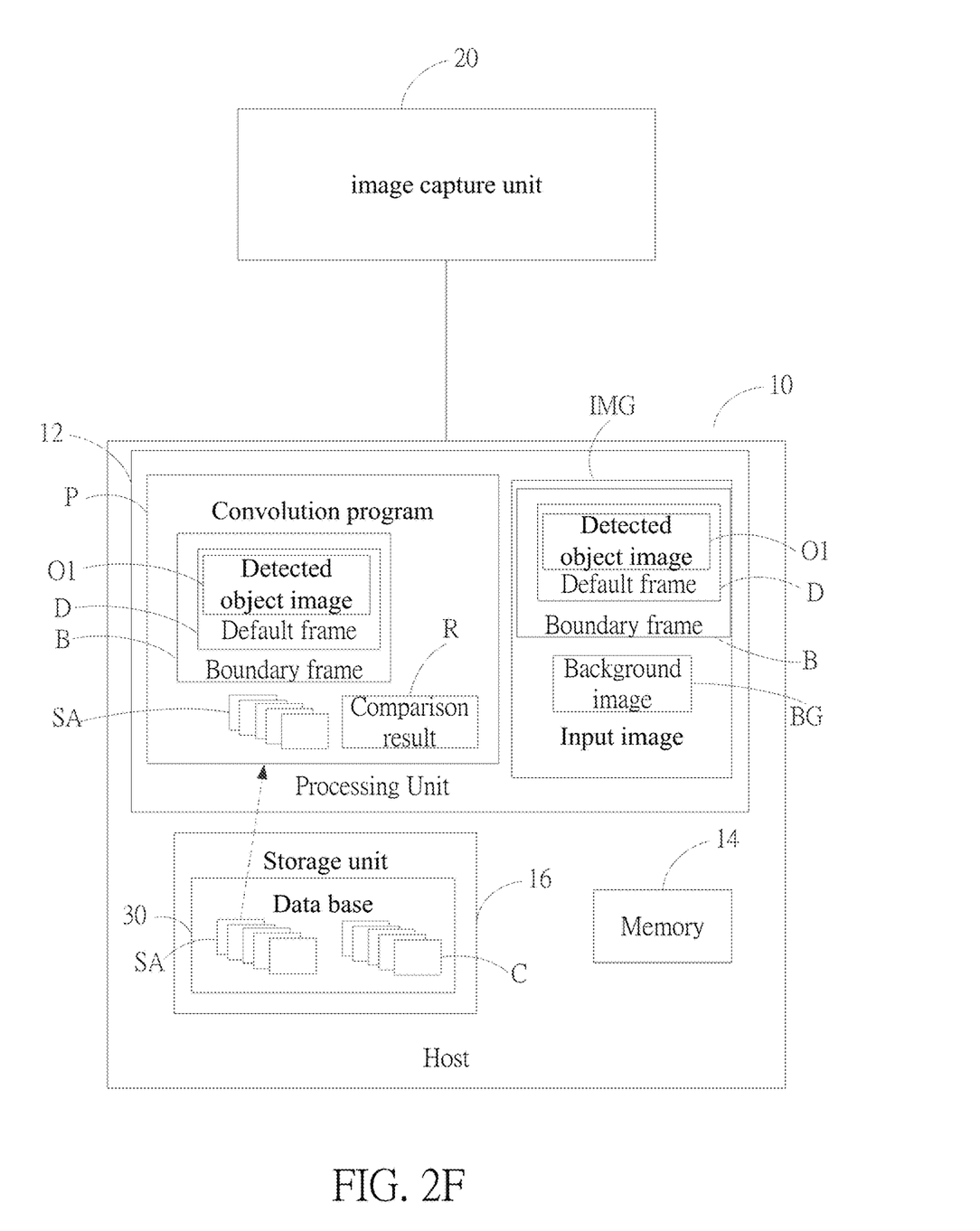
Figure 2G:
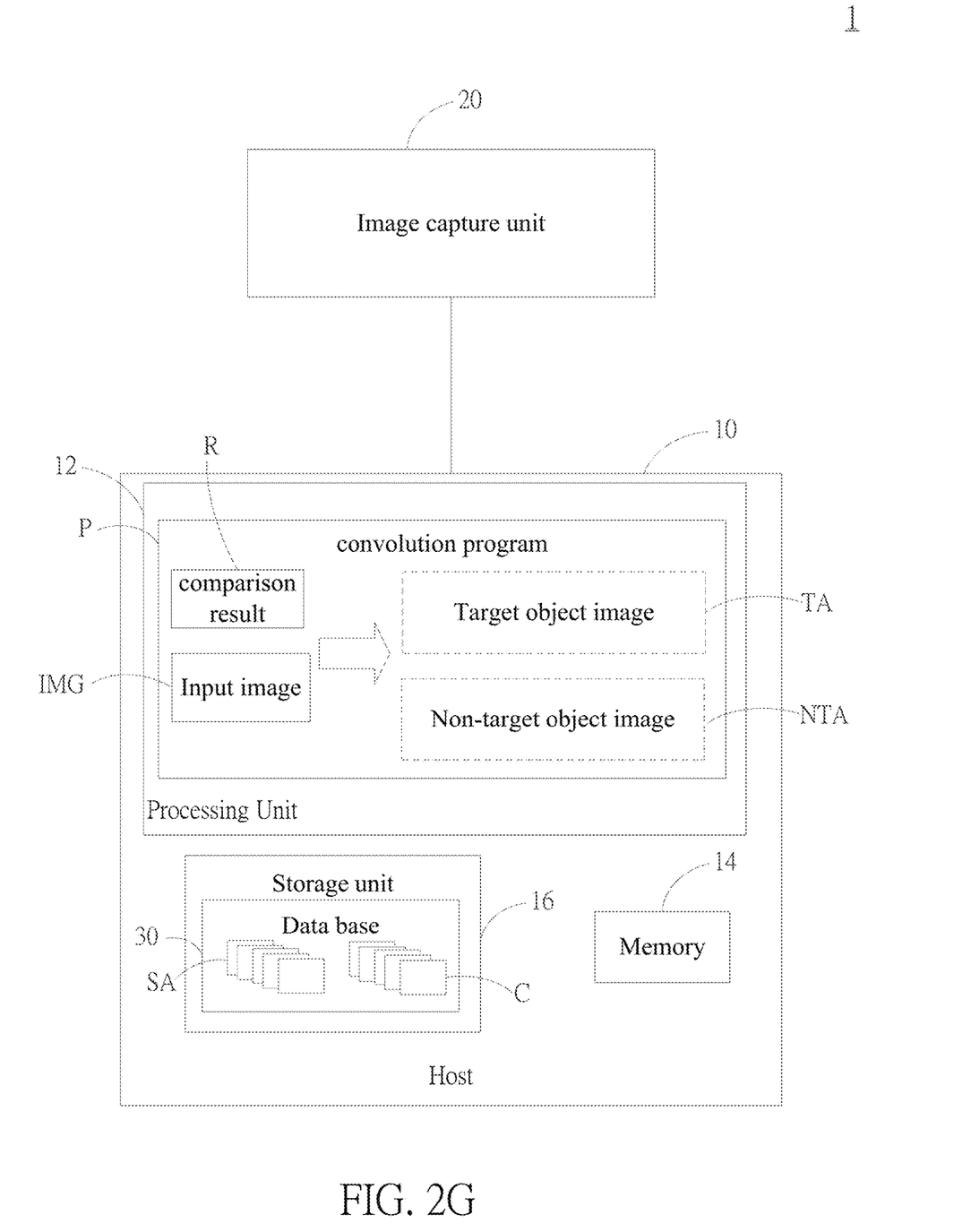

In Step S60, as shown in FIG. 2F, host 10 compares the detected object image O1 with the sample image SA in database 30 after locating the position of the detected object image O1 calculated by the processing unit 12, and obtains a comparison result R. continue to Step S70, as shown in FIG. 2G, through running the convolution program P executed by the processing unit 12, host 10 classifies the input image IMG into a target object image TA or a non-target object image NTA according to the comparison result R. For example, a malignant tumor. When the convolution program P executed by processing unit 12 of host 10 fails to identify at least one sample image SA from the detected object image O1 in frame D, host 10 classifies the input image IMG as the non-target object image NTA. Otherwise, the convolution program P executed by the processing unit 12 of host 10 classifies the input image into the target object image TA. Furthermore, when the convolution program P executed by the processing unit 12 of host 10 converts the input image into the non-target object image NTA, the convolution program P will continue to perform a second comparison between the sample image SA and the detected object image O1. When the convolution program P determines that the comparison result R of detected object image O1 is closer to the approximation threshold of one of the target object images TA (for example: When the approximation degree is between 0 and 1, and 0.5 is taken as the approximation threshold), the convolution program P will classify the input image IMG into the target object image TA, otherwise, the convolution program P would classify the input image IMG into the non-target object image NTA.

Figure 8:
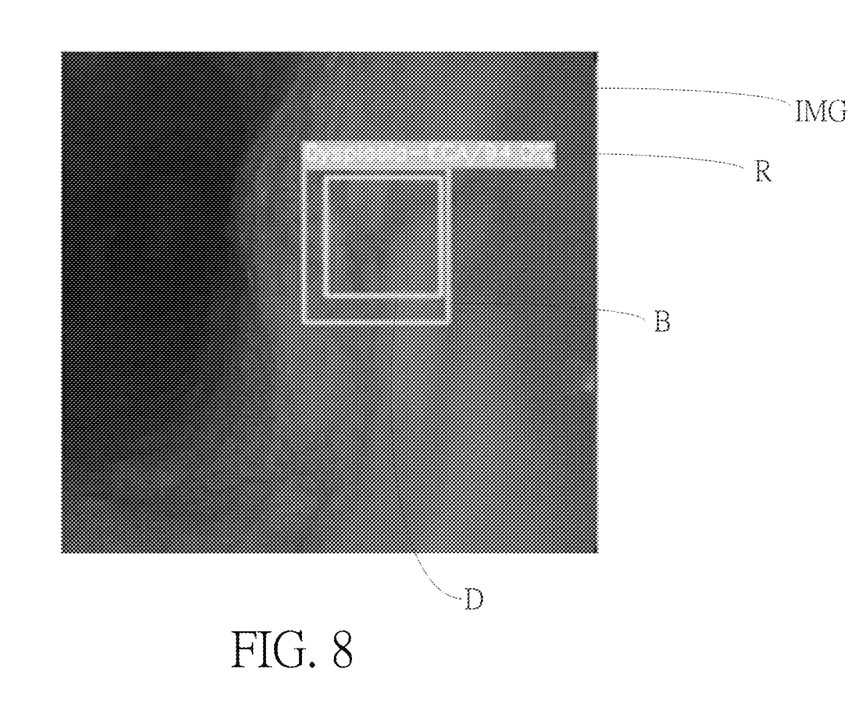
FIG. 8: which is a schematic diagram of superimposing the center points of default frame and boundary frame in the practical operation of the present application

As shown in FIG. 8, it is a schematic diagram of the present application's practical operation, in which the input image IMG is an esophageal endoscope image. For the input image IMG, the convolutional neural network (CNN) of the present application is used to detect the detected object image by superimposing the default frame D and the boundary frame B, and compare them to the sample image to obtain the comparison result R; the sample image is the esophageal endoscopic image in dysplasia area, so the approximation degree is 94.0%. For details, doctors need to carry out other medical diagnosis methods to diagnose the patient. Therefore, the present application can provide auxiliary evidence to doctors in judging the symptoms.

Sum up the aforesaid statements, the method of detecting a detected object image by a convolutional neural network provides a host to execute the convolution program and allow the host to build a Convolutional Neural Network, used to convolute the input image taken by the image capture unit to screen out the filter area under detection. A predicting detection frame is set up on the input image, and the position of the detected object image is located by the boundary frame through regression operation. Finally, perform the sample image comparison, and use the comparison result to classify the target object images and non-target object images according to the comparison result.

The invention claimed is:

1. A method for detecting an object image using a convolutional neural network, the steps include:
   Providing an input image to a host by an image capture unit, the input image including at least one detected object image and one background image;
   Converting the input image into a plurality of characteristic values and comparing the characteristic values with a plurality of convolution kernels to obtain at least one partial or full object image corresponding to some of the characteristic values by using the host, the convolution kernels containing the characteristic values of plural partial images and the adjacent background image in at least one object image;
   Capturing at least one regional image according to the region where the characteristic values corresponding to the partial or full detected object image and generating at least one default frame based on the edge of at least one regional image and overlapping the default frame on the input image, by using the host;
   Capturing and comparing a first center point of the default frames with a second center point of a boundary frame on the input image to obtain a center offset between the default frame and the boundary frames by using the host;
   Performing a regression operation according to the center offset to position the object image in the default frame on the input image by using the host, where the host performs the regression operation with a first position of the default frame, a second position of the boundary frame and a zooming factor to position the detected object image;
   Comparing the object image with at least one sample image to produce a comparison result by using the host; and
   Classifying the input image as a target object image or a non-target object image according to the comparison result by using the host;
   Wherein the boundary frame corresponds to the boundary of the input image, and thereby encompasses the entirety of the input image, and the default frame corresponds to the boundary of the detected object.

2. The method for detecting an object image with a convolutional neural network of claim 1, wherein in the step of Converting the input image into a plurality of characteristic values and comparing the characteristic values with a plurality of convolution kernels to obtain at least one partial or full object image corresponding to some of the characteristic values by using the host, the host sets the detection boundary of convolution cores to 3×3×p and normalizes a plurality of pixel values of input image to a plurality of pixel normal values; the host obtains the characteristic values in a convolution layer by having the convolution kernels multiplying the pixel normal values.

3. The method for detecting an object image with a convolutional neural network of claim 1, wherein in the step of capturing at least one regional image according to the region where the characteristic values corresponding to the partial or full detected object image, the host integrates the regions where the characteristic values are located, obtains the regional image of the input image, and establishes the default frame with the regional image.

4. The method for detecting an object image with a convolutional neural network of claim 1, wherein in the step of Converting the input image into a plurality of characteristic values and comparing the characteristic values with a plurality of convolution kernels to obtain at least one partial or full object image corresponding to some of the characteristic values by using the host, the host convolutes each pixel of input image according to a single shot multibox detector model to detect the characteristic values.

5. The method for detecting an object image with a convolutional neural network of claim 1, wherein in the step of comparing the detected object image with at least one sample image by using the host, the host performs classified comparison at a fully connection layer.

6. The method for detecting an object image with a convolutional neural network of claim 1, wherein in the step of classifying the input image as a target object image or a non-target object image based on a comparison result, when the host fails to identify the object image in the default frame that matches at least one sample image, the host classifies the input image as the non-target object image, else, the host classifies the input image as the target object image.

7. The method for detecting an object image with a convolutional neural network of claim 1, wherein in the step of classifying the input image as a target object image or a non-target object image according to a comparison result, when the host classifies the input image as the non-target object image, the host secondly compares at least one sample image with the object image; when the host judges that an approximation of one of the detected object images is greater than an approximation threshold, it classifies the input image into the target object image; else, the host classifies the input image into the non-target object image.

* * * * *